United States Patent [19]
Reitmeier et al.

[11] Patent Number: 5,693,839
[45] Date of Patent: Dec. 2, 1997

[54] PROCESS FOR STABILIZING HYDRIDIC SILANES

[75] Inventors: Rudolf Reitmeier; Lutz Rösch, both of Burghausen; Gilbert Geisberger, Altötting; Dieter Kippe, Burghausen, all of Germany

[73] Assignee: Wacker-Chemie GmbH, Munich, Germany

[21] Appl. No.: 806,751

[22] Filed: Mar. 3, 1997

[30] Foreign Application Priority Data

Apr. 25, 1996 [DE] Germany .................. 196 16 556.3

[51] Int. Cl.$^6$ .................................................. C07F 7/08
[52] U.S. Cl. ................................................... 556/401
[58] Field of Search ...................................... 556/401

[56] References Cited

U.S. PATENT DOCUMENTS 5,013,858  5/1991  Marquardt et al. .............. 556/401

OTHER PUBLICATIONS

L.G. Britton, "Combustion Hazards of Silane and its Chlorides", Part II, Mar. 1989, pp. 28–43, Union Carbide Corp.

*Primary Examiner*—Paul F. Shaver
*Attorney, Agent, or Firm*—Martin Connaughton

[57] ABSTRACT

In a process, according to the invention hydridic silanes such as $H_2SiCl_2$ or $SiH_4$ and oligomeric hydridic silanes containing up to 5 silicon atoms are admixed with a hydrocarbon stabilizer. The hydrocarbon may have functional groups selected from among carboxylic ester, aldehyde, keto, ether, thioether, tertiary amino, epoxy and cyano groups and halogen atoms.

9 Claims, No Drawings

PROCESS FOR STABILIZING HYDRIDIC SILANES

BACKGROUND OF THE INVENTION

Hydridic silanes which have an Si-H bond, are used in industrial technology not only for hydrosilylations to prepare donor silanes, but also for hydrogenation or reduction processes, gas-phase deposition processes such as CVD and for preparing very pure silicon for electronic applications, which starts with silicon contaminated by metals (metallurgical grade). The impurities present in the metallurgical raw silicon are removed by complicated pressure distillations of the trichlorosilane ($HSiCl_3$) or, in some processes, even the spontaneously inflammable monosilane ($SiH_4$) intermediate prepared from the metallurgical grade silicon. The "electronic grade trichloro-silane" obtained in this way tends to undergo Si—H/Cl exchange reactions which makes handling more difficult because the hydride-rich secondary silanes formed as a result of even a trace of HCl leads to increasing instability, particularly in contact with air. The ignition point of $HSiCl_3$ in accordance with DIN 51794 given in the safety data sheet, of about 185° C., can be lowered as far as room temperature on prolonged storage if significant amounts of spontaneously inflammable monosilane $SiH_4$ are formed.

An even more dangerous situation involves gaseous dichlorosilane $H_2SiCl_2$, whose ignition point according to production operation is between 70° C. and room temperature. This explosive by-product of the trichlorosilane synthesis is not isolated wherever possible, but passed during the production operation into tetrachlorosilane which is simultaneously formed in a larger amount. However, to ensure ignition points of above 200° C. for the $SiCl_4$ solutions, a high dilution to <3% of $H_2SiCl_2$ is necessary. L. G. Britton, "Combustion Hazards of Silane and its Chlorides", Part II, 1989, pp. 28–43, Union Carbide Corp., gives an ignition point of 44°±3° C. for very pure dichlorosilane. However, that reference does not describe an additive which would be suitable for significantly stabilizing the dangerous hydrogensilanes.

The oligomeric hydridic silanes have low ignition points. When ignition of mixtures containing hydrogensilane or oligomeric hydrogensilanes, particularly with air or oxygen, has occurred, the reaction usually propagates explosively.

BRIEF SUMMARY OF THE INVENTION

The present invention relates to a process for stabilizing hydridic silanes and oligomeric hydridic silanes containing up to 5 silicon atoms, wherein the hydridic silanes and oligomeric hydridic silanes are admixed with a hydrocarbon stabilizer.

DETAILED DESCRIPTION OF THE INVENTION

It is an object of the present invention to provide a process for stabilizing hydridic silanes and oligomeric hydridic silanes making the handling of these silanes easier and increasing their ignition points.

The present invention provides a process for stabilizing hydridic silanes and oligomeric hydridic silanes containing up to 5 silicon atoms, wherein the hydridic silanes and oligomeric hydridic silanes are admixed with hydrocarbon as a stabilizer which may have functional groups selected from among carboxylic ester, aldehyde, keto, ether, thioether, tertiary amino, epoxy and cyano groups and halogen atoms. For purposes of the invention, it should be understood that the hydrocarbon stabilizer may be a single hydrocarbon or mixture of hydrocarbons.

Hereinafter, the expression "hydridic silanes" will be used for both monomeric and oligomeric hydridic silanes.

The addition of the stabilizers increases the ignition point of the hydridic silanes and decreases the explosive power of silane-containing mixtures, in particular with air or oxygen, in the case of ignition. They effectively act as regulators in the free-radical chain mechanism and temper the force of the explosion which proceeds very violently without these stabilizers.

The stabilization has the advantage that it is relatively low cost and simplifies both handling and chemical operations involving hydridic silanes on an industrial scale. Cost savings begin in storage, where the safety precautions or larger tank volumes for dilution with $SiCl_4$ and/or inert gas which are necessary for silanes which are potentially spontaneously inflammable even at room temperature become unnecessary. The resulting higher ignition temperature class enables capital cost savings, particularly for chemical reactors, or the use of standard reactors.

Particular importance attaches to the stabilization of the monomeric hydridic silanes of the formula

$$R_bSiH_aX_c \quad (I)$$

and the oligomeric hydridic silanes of the formula

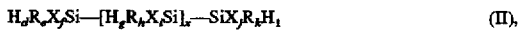

$$H_dR_eX_fSi-[H_gR_hX_iSi]_x-SiX_jR_kH_l \quad (II),$$

where, in the above formulae (I) and (II),

R is a hydrocarbon radical having from 1 to 18 carbon atoms which is optionally substituted with fluorine, chlorine or bromine atoms or cyano groups, X is a fluorine, chlorine or bromine atom or an alkoxy radical having from 1 to 18 carbon atoms which is optionally substituted by fluorine, chlorine or bromine atoms or cyano groups, a is 1, 2, 3 or 4, b, c, d, e, f, j, k and l are each 0, 1, 2 or 3, g, h and i are each 0, 1 or 2 and x is 0, 1, 2 or 3, with the proviso that, in formula (II), the sum of d+g+l is at least 1.

In formulae (I) and (II) above, all silicon atoms are tetravalent.

If the hydridic silanes contain halogen atoms, the halogen atom is the chlorine atom. In formulae (I) and (II), X are preferably either chlorine atoms or alkoxy radicals having from 1 to 6 carbon atoms which may be unsubstituted or substituted by fluorine, chlorine or bromine atoms or cyano groups, for example the methoxy, ethoxy, n-propoxy, isopropoxy, n-butoxy, iso-butoxy, sec-butoxy or tert-butoxy radical, pentoxy radicals such as the n-pentoxy radical and hexoxy radicals such as the n-hexoxy radical. The methoxy and ethoxy radicals are preferred. Preference is given to the unsubstituted alkoxy radicals.

Examples of the hydrocarbon radicals on the hydridic silanes, particularly R in formulae (I) and (II), are alkyl radicals such as the methyl, ethyl, n-propyl, iso-propyl, n-butyl, iso-butyl, tert-butyl, n-pentyl, iso-pentyl, neopentyl or tert-pentyl radical; hexyl radicals such as the n-hexyl radical; heptyl radicals such as the n-heptyl radical; octyl radicals such as the n-octyl radical and iso-octyl radicals such as the 2,2,4-trimethylpentyl radical; nonyl radicals such as the n-nonyl radical; decyl radicals such as the n-decyl radical; dodecyl radicals such as the n-dodecyl radical; octadecyl radicals such as the n-octadecyl radical; alkenyl radicals such as the vinyl and allyl radicals; cycloalkyl radicals such as cyclopentyl, cyclohexyl, cycloheptyl radicals and methylcyclohexyl radicals; aryl radicals such as the phenyl, naphthyl, anthryl and phenanthryl radicals; alkaryl radicals such as o-, m- and p-tolyl radicals, xylyl radicals and ethyl-phenyl radicals; and aralkyl radicals such as the benzyl radical, the α- and the β-phenylethyl radical.

Examples of substituted hydrocarbon radicals R are cyanoalkyl radicals such as the β-cyanoethyl radical, and halogenated hydrocarbon radicals, for example haloalkyl radicals such as the 3,3,3-trifluoro-n-propyl radical, the 2,2,2,2',2'-hexafluoroisopropyl radical, the heptafluoroisopropyl radical and haloaryl radicals such as the o-, m- and p-chlorophenyl radicals.

Preference is given to the above-mentioned unsubstituted hydrocarbon radicals having from 1 to 6 carbon atoms, in particular the alkyl radicals and the phenyl radical.

In formulae (I) and (II), it is preferred that a is 2, 3 or 4, x is 0, 1 or 2 and the sum of d+g+1 is at least 1, 2 or 3.

Particularly important stabilizable hydridic silanes are dichlorosilane, trichlorosilane, methylsilane $CH_3SiH_3$, and monosilane $SiH_4$, and also the disilanes $H_3Si$—$SiH_3$ and $HSiCl_2$—$SiCl_3$.

Stabilizers which are used can be saturated and unsaturated hydrocarbons. The hydrocarbons have, in addition to any above-mentioned functional groups, from 1 to 30, preferably from 1 to 18, more preferably from 2 to 12, carbon atoms.

Examples of hydrocarbons are saturated alkanes such as linear or branched paraffins, e.g. gasoline distillation fractions, and cyclo compounds such as cyclohexane or alkyl-substituted cyclic hydrocarbons.

Examples of saturated alkanes having functional groups are tert-butyl chloride or iso-butyl chloride, isopropyl chloride, amyl chloride, methyl tert-butyl ether, tetrahydrofuran or dibutyl ether.

Aromatic and unsaturated aliphatic hydrocarbons are preferred as stabilizers because they produce a large increase in the ignition point of the hydridic silanes.

Examples of aromatics and alkylated aromatics are benzene, toluene, xylenes or heteroaromatics, in particular halogen-substituted compounds such as chlorobenzene. They are preferred because they do not hinder a hydrosilylation of the hydridic silanes using platinum catalysts.

Particularly effective are unsaturated aliphatic hydrocarbons having isolated double or triple bonds, for example ethene, propene, allyl chloride, isobutene, n-butene or relatively long-chain olefins, propyne or phenylacetylene. Preference is given to internal or cyclic olefins such as 2-methyl-2-butene, 2-butene, esters of crotonic acid, cyclopentene, cyclohexene, cyclooctene or cyclooctadiene.

The stabilizers are used in amounts of from 1000 to 0.01 parts by weight, preferably from 500 to 0.1 parts by weight, per 100 parts by weight of hydridic silanes.

Internal olefins such as 2-methyl-2-butene lead, even at very small amounts of stabilizer such as less than 1 part by weight per 100 parts by weight of hydridic silanes, to high stabilization which does not decrease by addition onto the double bond even in the presence of hydrosilylation catalysts. The effective stabilizers cyclopentene, cyclohexene or isobutene are preferred in hydrosilylation processes where they simultaneously serve as reaction partner to the respective hydridic silane. To ensure reliable stabilization over all phases of the addition process, preference is given to at least the molar amount of olefin corresponding to the respective number of moles of hydridic silanes.

The stabilizers used in a small amount can be selected such that they give efficient stabilization but do not hinder the planned chemical reaction. In hydrosilylations, they must not cause long-term inhibition of the noble metal catalyst nor contribute significantly to elimination of $H_2$ from the hydridosilane.

The stabilizers can be added before or during the formation of the hydridic silanes to be stabilized. The stabilizers can be added to hydridic silanes which can dismute as a result of ligand exchange and form silanes richer in hydride or even $SiH_4$. The process for stabilization is well suited to safe transport and prolonged storage of such hydridic silanes.

When using the hydridic silanes in hydrosilylations, the stabilizer is initially charged directly into the container such as a storage tank or pressure vessel into which the hydridic silanes are to be placed. This avoids safety problems from the beginning, even in the presence of catalysts which can contribute to the otherwise dangerous H/X ligand exchange on the silicon by dismutation or disproportionation.

The stabilizers can also be held ready outside the container in which the hydridic silanes are located in case the hydridic silanes are to be stabilized.

The stabilizers can be added only when necessary, e.g. if the internal temperature approaches the ignition point or the ignition point is lowered by H/Cl exchange and/or contact with air is to be expected, in the case of leakages of hydridic silanes or when a storage tank or a pipe has to be opened or emptied. This makes it possible to carry out CVD processes or other deposition processes using pure hydridic silanes without stabilizers being introduced directly into the hydridic silane to be deposited. The boiling point of the stabilizers being held ready is at most 30°, preferably at most 10° greater then the boiling point of the hydridic silanes.

It is sufficient to simply add or pump the respective stabilizer into the container holding the hydridic silane or a mixture comprising hydridic silanes. Since hydrocarbons, in particular unsaturated hydrocarbons, mix sufficiently with the silanes to be stabilized, additional mixing, e.g. by means of stirring, is not necessary.

In the case of gaseous hydridic silanes such as $SiH_4$, the vapor pressure of liquid olefins added is sufficient to give significant stabilization of the gas which is otherwise spontaneously inflammable even at low temperatures. An additional solvent is not necessary, but can be present at any time.

In the examples below, unless otherwise indicated, a) all indications of amounts are by weight;

b) all pressures are 0.10 MPa (abs.);

c) all temperatures are 20° C.;

d) the ignition points of the mixtures on contact with air are measured in accordance with DIN 51794, corresponding to EC method A.12 (directive 84/449/EC).

EXAMPLES a) Stabilization of Dichlorosilane

Example 1

Saturated hydrocarbon as stabilizer

A cylindrical 0.9 l Parr pressure vessel fitted with a pressure gauge and a needle valve in the gas space installed as gas discharge is charged at room temperature with 360 g of aromatics-free methylcyclohexane. A total of 240 g of a 99% pure dichlorosilane from a pressure can of stainless steel, in which a gauge pressure of about 0.15 MPa prevails, hereinafter referred to as the reservoir can, are then introduced into the lower part of the pressure vessel via a second feed point which is provided with a submerged tube and can be closed by means of a further needle valve.

This gives a 40% strength stable and readily handlable solution of $H_2SiCl_2$ in methylcyclohexane. A sample taken via the submerged tube gives an ignition point of 250° C. which is thus about that of pure methyl-cyclohexane.

A gauge pressure of about 0.01 MPa can be measured at room temperature over the almost saturated solution. The samples taken from the gas space through the gas discharge valve similarly display ignition points of from 180° C. to 190° C.

COMPARATIVE EXAMPLE

Dilution of dichlorosilane with $SiCl_4$ (not according to the invention)

A 25% strength solution of dichlorosilane in tetrachlorosilane prepared using the same procedure as in Example 1 gives a comparatively low initial ignition point of 90° C. Ignition occurs with high explosive force. After storage for 1 week, the ignition point drops to from 80° to 70° C. After an additional 1–3 weeks, there is so much monosilane in the Parr vessel that the silane mixture flowing out at the gas discharge immediately ignites spontaneously, i.e. without additional supply of energy, to form a narrow flame.

Further dilution of the initially prepared 25% strength $H_2SiCl_2$ solution with $SiCl_4$ gives ignition points of only about 115° C. at 10% strength and finally about 195° C. at 3% by weight of $H_2SiCl_2$ in tetrachlorosilane. This high dilution is of little interest for industrial syntheses.

Example 2

Stabilizers for $H_2SiCl_2/SiCl_4$ solution

If only 1 part by weight of 2-methyl-2-butene is added to 99 parts of the 25% strength solution of $H_2SiCl_2$ in tetrachlorosilane described in the comparative example above, the ignition point of the mixture thus stabilized is increased to 240° C.

The table below shows some stabilizers which similarly lead to stabilization of the resulting dichlorosilane solutions.

| Parts by weight | | | |
|---|---|---|---|
| $H_2SiCl_2$ | $SiCl_4$ | Parts by weight (P) of stabilizer | Ignition point |
| 25 | 75 | — | 80° C. after 1 week |
| 25 | 75 | 1 P 2-methylbutene | 240° C. |
| 25 | 75 | 5 P 2-methylbutene | 330° C. |
| 20 | 58 | 2 P toluene | 280° C. |
| 24 | 71 | 5 P petroleum[1] | 190° C. |
| 23 | 71 | 6 P cyclohexane | 200° C. |
| 24 | 71 | 4 P MTBE[2] | 210° C. |
| 23 | 68 | 8 P 2-Cl-Me-propane[3] | 220° C. |
| 25 | 75 | 1 P cyclooctene | 230° C. |

[1]Petroleum = petroleum ether fraction (bp. 60–70° C.)
[2]MTBE = tert-butyl methyl ether
[3]2-Cl-2-Me-propane = tert-butyl chloride Subsequent measurements show that the high values measured remain stable over a number of weeks to months.

Example 3

Addition of olefins to technical grade dichlorosilane

A 0.9 l Parr pressure vessel, as described in Example 1, is charged with 2 g of cyclopentene and, with exclusion of oxygen and moisture by means of argon flushing, a total of 305 g of technical grade $H_2SiCl_2$ (99% pure) from the 10 l reservoir can is introduced.

The ignition point of the gas mixture which can be taken from the discharge valve on the cover plate of the cylindrical pressure vessel is >160° A subsequent measurement afar storage for 1 month in the Parr vessel again gives 160° C. as the ignition point, although it is noticeable that Cl/H exchange has already taken place by disproportionation. The gas chromatogram shows, apart from $H_2SiCl_2$, a few % of $H_3SiCl$ or $HSiCl_3$ as main constituents.

A dichlorosilane charge stored in parallel thereto without stabilizer in a similar pressure vessel is, owing to the Cl/H exchange reaction, spontaneously inflammable when taken off in gas form via the needle valve, i.e. at room temperature, and leads to a narrow flame. Addition of 2% by weight of 2-methyl-2-butene increases the ignition point back to safe values of >200° C.

Example 4

Cyclopentene/$H_2SiCl_2$ mixture, hydrosilylation 245 g of cyclopentene are initially placed in a 1 l stirring autoclave fitted with discharge valve and 304 g of $H_2SiCl_2$ are then pumped in via a submerged tube reaching into the organic phase. From the resulting about 54% strength dichlorosilane/cyclopentene solution, about 50 g are taken off under inert conditions (dried, evacuated receiver, stainless steel capillary with screw connection, argon flushing) via the discharge valve for the ignition point determination. Values of >230° C. are obtained.

The monoaddition of cyclopentene is initiated by adding a catalyst solution derived from hexachloroplatinic acid and heating. After a reaction time of about 10 minutes, the mixture is quickly cooled and a 2nd sample is taken off for the ignition point determination. The measurement now gives 240° C.

After the reaction mixture has again been heated in the autoclave and has finally been reacted substantially to the desired monoaddition product cyclopentyldichlorosilane, a 3rd ignition point determination gives values of from 240° to 250° C.

Example 5

Isobutene/dichlorosilane

Using a method similar to Example 4, 350 g of isobutene are first placed in the 1 l autoclave. After addition of 270 g of dichlorosilane and stirring, the internal pressure which is established in the autoclave again enables liquid dichlorosilane/isobutylene mixture to be taken off via the bottom valve into a smaller, evacuated pressure vessel. The ignition point of this liquefied gas mixture is 250° C.

The main part of the isobutylene/dichlorosilane mixture remaining in the autoclave is reacted by addition of a homogeneous platinum catalyst to give the desired diisobutyldichlorosilane in high selectivity. The silane has an ignition point of 280° C.

b) Stabilization of other Hydridic Silanes:

Example 6

Stabilization of trichlorosilane

Addition of 3% of tert-butyl chloride to pure $HSiCl_3$ (ignition point: 185° C.) reliably stabilizes the ignition point to values of >220° C., so that a significantly simpler design of the plants for further processing according to the temperature class T3 is now sufficient, instead of the complicated and expensive T4 equipment.

A comparable stabilization of technical grade trichlorosilane is obtained by addition of about 1% by weight of olefins. In the case of hydrosilylations, the olefinic reactant, e.g. isobutene, octene or diisobutylene, is preferably initially charged or added in the % range to the $HSiCl_3$

Example 7

Stabilization of monosilane $SiH_4$

Using a procedure similar to that in Example 1, 223 g of 2-methyl-2-butene are first placed in the dried and evacuated 0.9 1 Parr pressure vessel. 25 g of $SiH_4$ are then injected via the submerged tube, corresponding to 10.1% of $SiH_4$. A gauge pressure of 0.9 MPa is measured. The ignition point determination for the liquid taken off via the submerged tube gives a value of 350° C. The sample taken from the gas space has an ignition point of >190° C.

For an initial charge of 200 g of cyclopentene (Cp) and 8.4 g of injected $SiH_4$ (corresponding to 4.2% of $SiH_4$; the gauge pressure is measured as 0.4 MPa), ignition points found for the liquid Cp phase are 300° C., and again 190° C. for the gas space.

The ignition process is here significantly more moderate than for pure $SiH_4$, which like the pure $H_2SiCl_2$ or the $SiCl_4$ solution ignites very violently. The relatively low concentration of unsaturated stabilizer, which, particularly in the gas phase, corresponds to the very different vapor pressures, is sufficient to moderate the oxidation process so as to avoid dangerous situations. The $SiH_4$ gas flowing out from the upper discharge displays no violent reaction. If it is passed over a naked flame, it burns very moderately. This forms very light long threads which stick together when they are wound up.

The liquid remaining after blowing off the overpressure shows, even in air, no conspicuous differences from the solutions obtained in the examples above.

Example 8

Stabilization of organohydridosilanes

As in Example 7, 226 g of 2-methyl-2-butene are first placed in the 0.9 1 pressure vessel and 23.4 g of gaseous methylsilane $CH_3SiH_3$ are then passed in. This corresponds to 9.4% of $CH_3SiH_3$. The gauge pressure measured is 0.2 MPa. The ignition point of the sample taken via the submerged tube is >230° C. This represents a significant stabilization compared with the pure $CH_3SiH_3$ whose ignition point is 160° C.

Addition of 5% by weight of 2-methyl-2-butene also stabilizes hydridic silanes formed in situ, e.g. hydridic silanes formed in the H-transfer from $CH_3SiH_3$ to organosilanes $RSiCl_3$ or $R_2SiCl_2$. Although this or the distillation forms explosive polyhydridosilane by-products detectable by gas chromatography or NMR (e.g. $PhSiH_3$ and $SiH_4$ in addition to $PhSiHCl_2$ in the hydrogenation of phenyltrichlorosilane), the ignition point of the reaction mixture containing 5% of olefinic stabilizer always remains above 230° C.

Example 9

Hydridic silanes having Si-Si bonds

The residue remaining after separating off $HSiCl_3$ and $SiCl_4$ by distillation from the crude silane mixture from the industrial trichlorsilane synthesis contains hexachlorodisilane and hexachlorodisiloxane as well as some hydridic chlorodisilanes and also longer-chain silanes which make this residue very explosive, particularly in the presence of air or oxygen.

The ignition temperature of a typical residue from the trichlorosilane synthesis having a total H content of 0.2% by weight (according to $^{29}$Si-NMR: about 12% of $HSi_2Cl_5$, 9% of $H_2Si_2Cl_4$ plus higher molecular weight H-containing chlorosilanes) is 60° C. without stabilizer. It undergoes a violent oxidation.

The simple addition of 8% by weight of 2-methylbutene to a sample of this residue increases the ignition point of the mixture to above 200° C. The analogous addition of 10% by weight of chlorobenzene to the residue gave an ignition point of >150° C. The residue mixtures stabilized with these organic additives burned quite moderately.

Addition of unsaturated organic stabilizers thus also makes hydridic disilanes and polysilanes safe to store and also to dispose of or to incinerate.

What is claimed is:

1. A process for stabilizing hydridic silanes and oligomeric hydridic silanes containing up to 5 silicon atoms, wherein the hydridic silanes and oligomeric hydridic silanes are admixed with a hydrocarbon stabilizer, wherein said hydrocarbon optionally has functional groups selected from the groups consisting of a carboxylic ester, aldehyde, keto, ether, thioether, tertiary amino, epoxy and cyano groups and halogen atoms.

2. The process as claimed in claim 1, wherein the monomeric hydridic silanes have the formula

and the oligomeric hydridic silanes have the formula

where, in the above formulae (I) and (II),

R is a hydrocarbon radical having from 1 to 18 carbon atoms which is optionally substituted with fluorine, chlorine or bromine atoms or cyano groups, X is a fluorine, chlorine or bromine atom or an alkoxy radical having from 1 to 18 carbon atoms which is optionally substituted with fluorine, chlorine or bromine atoms or cyano groups, a is 1, 2, 3 or 4, b, c, d, e, f, j, k and l are each 0, 1, 2 or 3, g, h and i are each 0, 1 or 2 and x is 0, 1, 2 or 3, with the proviso that, in formula (II), the sum of d+g+1 is at least 1.

3. The process as claimed in claim 2, wherein R is an unsubstituted hydrocarbon radical having from 1 to 6 carbon atoms.

4. The process as claimed in claim 2, wherein X is a chlorine atom or alkoxy radical having from 1 to 6 carbon atoms.

5. The process as claimed in claim 1, wherein the stabilizer is a hydrocarbon having from 1 to 18 carbon atoms.

6. The process as claimed in claim 1, wherein the stabilizer is present in amounts of from 1000 to 0.01 parts by weight per 100 parts by weight of hydridic silanes and oligomeric hydridic silanes.

7. The process as claimed in claim 1, wherein the stabilizer is an aromatic or unsaturated aliphatic hydrocarbon.

8. The process as claimed in claim 1, wherein the stabilizer is added to the hydric silanes as the temperature of the hydric silanes approaches its ignition point.

9. The process as claimed in claim 8, wherein the boiling point of the stabilizer is at most 30° different from the boiling point of the hydridic silanes.

* * * * *